United States Patent [19]

Detriché et al.

[11] Patent Number: 4,651,093
[45] Date of Patent: Mar. 17, 1987

[54] MULTIPLE COIL EDDY CURRENT PROBE EQUIPPED WITH A COIL BALANCING DEVICE

[75] Inventors: Jean-Marie Detriché, Saint-Germain-en-Laye; Didier Houche, Vendome; Laurent Gachet, Paris, all of France

[73] Assignee: Commissariat a l'Energie Atomique, Paris, France

[21] Appl. No.: 577,149

[22] Filed: Feb. 6, 1984

[30] Foreign Application Priority Data

Feb. 8, 1983 [FR] France .................................. 83 01951

[51] Int. Cl.⁴ ...................... G01N 27/87; G01N 27/90; G01R 33/12
[52] U.S. Cl. .................................... 324/232; 324/233; 324/238
[58] Field of Search ......................... 324/232, 233–243

[56] References Cited

U.S. PATENT DOCUMENTS

| | | | |
|---|---|---|---|
| 3,611,121 | 10/1971 | Vild et al. | 324/238 |
| 3,823,368 | 7/1974 | Mansson et al. | 324/40 |
| 4,424,486 | 1/1984 | Denton et al. | 324/233 X |
| 4,467,281 | 8/1984 | Davis et al. | 324/232 |

FOREIGN PATENT DOCUMENTS 2424515 11/1979 France .
2507310 12/1982 France .

Primary Examiner—Gerard R. Strecker
Attorney, Agent, or Firm—Pearne, Gordon, McCoy & Granger

[57] ABSTRACT

The invention relates to a multiple coil eddy current probe equipped with a coil balancing device. This probe comprises several coils forming an eddy current probe supplying in each case one signal. Each coil is regulated to overvoltage by a regulating unit, which acts on the frequency of the high frequency oscillator supplying each coil. Application is to the automatic positioning of a welding torch and to the inspection of the weld.

8 Claims, 6 Drawing Figures

MULTIPLE COIL EDDY CURRENT PROBE EQUIPPED WITH A COIL BALANCING DEVICE

BACKGROUND OF THE INVENTION

The present invention relates to a multiple coil eddy current probe equipped with a coil balancing device. As a non-limitative example, the invention relates to the problem of determining, with the aid of juxtaposed coils arranged in rows or matrixes, the profile of the joint separating two parts to be welded, in order to control the automatic positioning of a member, such as a welding torch relative to the joint or vary certain welding parameters as a function of the detected profile. However, this application is not limitative and the invention can also be used for determining the profile of all conductive metal surfaces or for carrying out the non-destructive inspection of such surfaces. It can also apply to non-juxtaposed coils for supplying comparable information.

The principle of an eddy current probe consists of supplying a coil with a high frequency sinusoidal electric current, so as to produce an alternating field which induces, in an electricity-conducting member facing the probe, eddy currents producing during their return path a field which opposes the initial field and modifies the impedance of the coil. The variations of the impedance of the coil give an indication of the arrangement of the coil with respect to the facing part and the particular profile of said part. This generally relates to information on the distance separating the coil from the part in the case of a probe used in proximity. It can involve information on the structure of the part in the case of a probe used in non-destructive inspection.

An eddy current probe can have one or more coils. In the case of a probe with a single coil, the detection of a profile of a part or a non-destructive inspection of said part requires means for carrying out mechanical scanning of the part by the coil. In the case of a multiple coil probe, this mechanical scanning is often replaced by an electronic scanning of the juxtaposed coils, which in each case supply a point of the profile to be determined. Such a device is often preferable to a device with a single coil, in which the mechanical scanning introduces vibrations into the probe, which are prejudicial to the accuracy of the measurement.

In general terms, the sensitivity of the measurement is at a maximum, when the coils are regulated to overvoltage or resonance. Thus, the eddy current probes are provided with means for regulating each coil to overvoltage.

It is well known that the sensitivity of such a probe is at its maximum when the circuit is tuned to resonance. This state of resonance is defined by the relation $LC\omega^2 = 1$ where L is the overall inductance of the circuit (mainly the coil), C is the overall capacitance of the circuit, and $\omega = F/2\lambda$, where F is the frequency of the sinusoidal signal delivered by the oscillator. It is also well known that, when a resonant circuit is tuned to resonance, the voltage across the inductance (i.e. the coil) is greater than the voltage of the signal delivered by the oscillator. So, it is said that the coil is in an overvoltage state. Therefore, as used herein, "coils regulated to overvoltage" means that the resonant circuit is tuned to resonance, in order to have the greatest sensitivity.

The most frequently used regulating means consists of using, for each coil, a variable resistance—capacitance network, connected to one end of the coil on the one hand and to earth on the other. The disadvantage of this solution is that it requires the same number of resistance—capacitance networks as there are coils, which can involve several dozen networks and the same number of controls on the probe.

The use of several juxtaposed coils, which may optionally be organized in matrix-like manner, is difficult due to the magnetic interaction between adjacent coils. Thus, the signal supplied by one coil can be affected by the supply to adjacent coils, which makes it difficult to simultaneously balance all the coils.

French Pat. No. 79 10458, filed on Apr. 25th 1979 provides a solution to this problem of supplying the coils, by proposing a sequential excitation thereof. This invention also proposes the use of the same number of processing means for the signals from the coils as there are coils, which increases the number of circuits and consequently increases the cost of the apparatus and reduces its reliability.

French Pat. No. 81 11087, filed on June 4th 1981 provides an improvement to the aforementioned patent. The coils are excited in parallel and supply signals to a multiplexer connected to a single processing means. Thus, processing takes place sequentially on each of the signals of the coils. The use of a single processing means consequently makes it possible to simplify the apparatus, but the latter is still difficult to balance, because it is necessary to adjust the variable resistance—capacitance network of each coil in such a way that each of the coils is regulated to overvoltage. The expert uses here miniaturized variable air capacitance positioned as close as possible to the coils and whose variation range is a few percent, which is not always sufficient for completely carrying out the disparities in the characteristics of the various coils which, by design, may differ by more than 10%.

SUMMARY OF THE INVENTION

The object of the present invention is to obviate these disadvantages by supplying an apparatus having an eddy current probe, equipped with means for regulating each coil, which has high dynamics and which is therefore easy to use.

This objective is achieved by the use of means for exciting the coils which supplies each coil with an excitation signal, whose frequency differs between the individual coils. The excitation frequency of one coil is dependent on the characteristics of the coil and of the resistance—capacitance network associated therewith. This excitation frequency is such that the coil is regulated to overvoltage or resonance.

More specifically, the present invention relates to a multiple coil eddy current probe equipped with a device for balancing the coils incorporating a plurality of coils, a balancing circuit for each coil, a high frequency oscillator for exciting each coil, at least one means for processing the signals at the terminals of each coil, a plurality of means for storing the processed signals, each storage means being associated with a coil, switching means between said different means and means for controlling the switching means.

According to the invention, the balancing circuit comprises at least one resistance—capacitance network and one means for regulating each coil acting on the frequency of the electric signal supplied by the high frequency oscillator and the control means acts on the switching means in such a way that at each instant a single storage means is addressed, said storage means receiving, across a processing means, the signal supplied by the coil regulated to overvoltage and connected to earth across its resitance—capacitance network.

Numerous different embodiments of said probe are possible. These embodiments are linked with the nature of the electrical connections and in particular the presence or absence of multiplexer or demultiplexer-type switching means between two means of the probe. These switching means can be positioned between the oscillator and the coils, between the coils and the measuring points, between the coils and earth, and between the measuring points and the processing means, a measuring point being a point at which is sampled the signal supplied by a coil for application to a processing means.

The oscillator—coil connection can either be direct, the oscillator being connected to all the coils, or can be realized by a demultiplexer. The coil—measuring point connection can either be direct, or can be realized by a multiplexer. In both cases, there can be a single measuring point (interconnected coils or measuring point taken on the output of the multiplexer), or not (non-interconnected coils or measuring points taken on the inputs of the multiplexer). The coil—earth connection can either be direct if the resistance—capacitance network associated with each coil is permanently connected to earth, or multiplexed if these networks are connected to the inputs of a multiplexer, whose output is connected to earth. In the first case, there is a single resistance—capacitance network if the bases of the coils are interconnected. Finally, the measuring point—processing means connection can either be direct, a processing means being connected to each measuring point, or multiplexed. In the latter case, the multiplexer can be replaced by an adder, the choice of measuring channel being made by a preceding multiplexing.

The various possible combinations between the direct or multiplexed connections define the same number of multiple coil probe embodiments. However, certain combinations correspond to inoperative arrangements. For example, this is the case if simultaneously the oscillator—coil connection is direct, the coil—measuring point connection is direct (not a single measuring point), the coil—earth connection is direct and the measuring point—processing means connection is direct.

Obviously the invention only relates to the multiple coil probes obtained by a combination of switching means which can be controlled in such a way that at all times a single storage means is addressed, said storage means receiving, across a processing means, the signal supplied by a coil regulated to overvoltage and connected to earth across its resistance—capacitance network.

According to the invention, the balancing circuit regulating means comprises a switch, whose output is connected to the high frequency oscillator and whose inputs, whose number is equal to the number of coils, are connected to regulating units.

According to a secondary feature, the regulating units are variable resistors.

According to another secondary feature, the regulating units are variable capacitors.

BRIEF DESCRIPTION OF THE DRAWINGS

The invention is described in greater detail hereinafter relative to non-limitative embodiments and the attached drawings, wherein show.

DETAILED DESCRIPTION OF THE INVENTION

Figure 1:
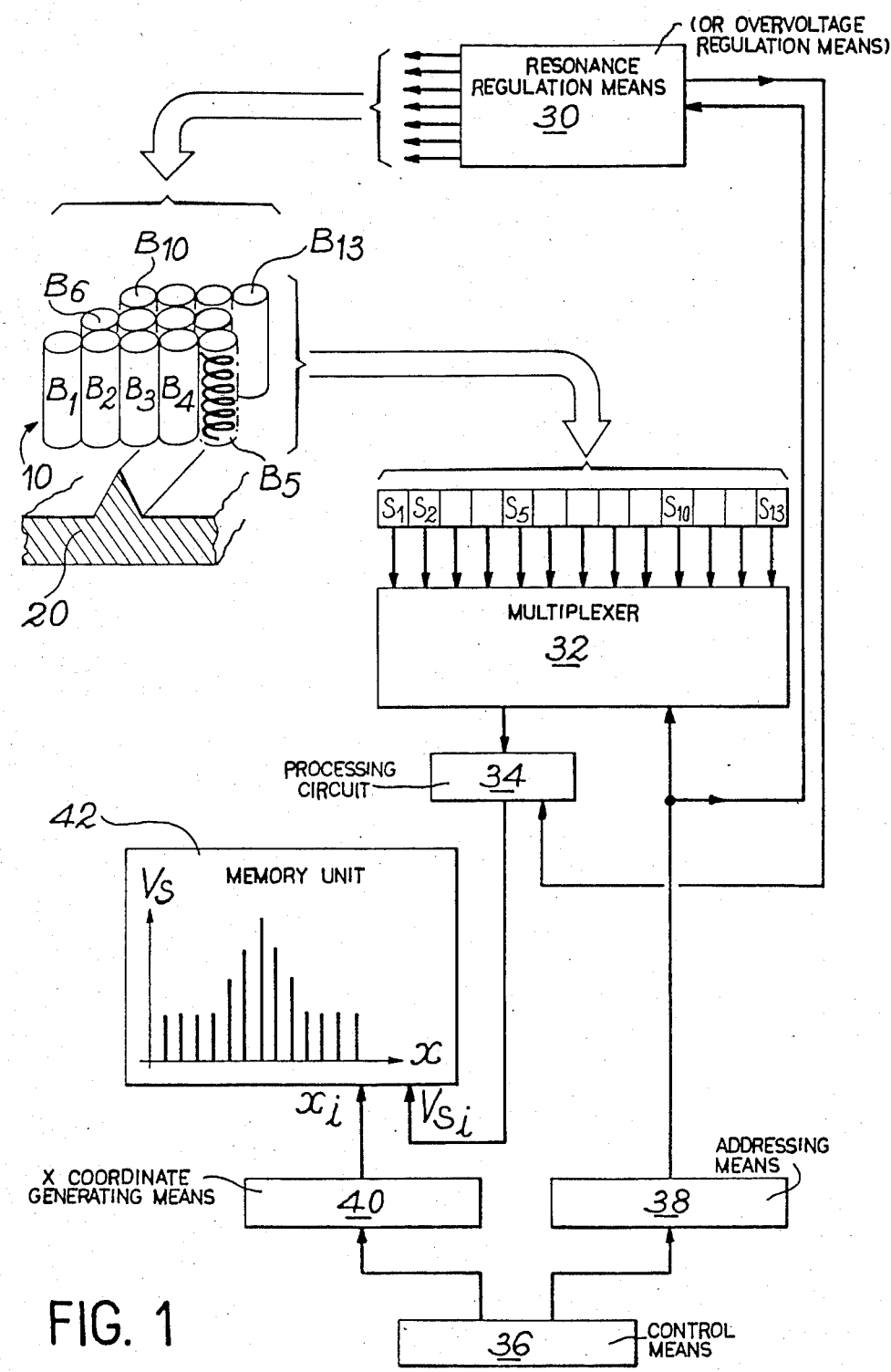
FIG. 1 diagrammatically a multiple coil eddy current probe according to the invention used in the determination of the profile of the surface.

FIG. 1 shows the case of a multiple coil eddy current probe 10 used for detecting the profile of the surface 20 of a conductive part.

This probe comprises a switching means between the oscillator and the coils and another switching means between the measuring points, whose number is equal to the number of coils, and a single processing means. The coil—earth connection is not shown. These switching means permit a sequential excitation of each coil.

For example, this probe comprises 13 coils $B_1$ to $B_{13}$ arranged in three staggered rows. These three rows of coils are close to one another, in such a way that probe 10 detects the profile of a line of surface 20 parallel to one row of coils, rather than an area of said surface 20. It is obvious that the use of several staggered rows of coils makes it possible to increase the resolution of probe 10 because on a probe 10 of given length, which is equal to the distance between the centres of the coils $B_1$ to $B_5$, there are the same number of coils as there are rows.

According to the invention, these coils $B_1$ to $B_{13}$ are individually regulated to the overvoltage or resonance by a means 30, which comprises a high frequency oscillator sequentially supplying the coils and whose frequency is adjusted to an appropriate value for each coil. The signals $S_1$ to $S_{13}$ sequentially supplied to each of the coils $B_1$ to $B_{13}$ of probe 10 are applied to the input of a multiplexer 32 used as a switch. The latter successively injects each of these signals $S_1$ to $S_{13}$ into a single processing circuit 34, which also receives a reference signal from means 30. A control means 36 simultaneously makes it possible, via a circuit 38, to carry out the addressing of multiplexer 32 and means 30, which carries out the addressing of a coil $B_i$ of probe 10. Processing circuit 34 then supplies a signal $V_{Si}$, which is stored in a memory unit 42. Control means 36 also activates a circuit 40 which activates into the memory unit 42 and in parallel with signal $V_{Si}$, a signal $x_i$, which takes account of the position of coil $B_i$. The scanning of all the coils carried out in this way by a series of 13 pulses under the action of control means 36, due to multiplexer 32 and means 30, leads to the introduction into memory unit 42 of the image profile of the object profile facing the probe.

FIG. 1 shows that the image profile appearing in the memory unit 42 is not identical to the real profile of surface 20 facing probe 10. This difference is due to the non-linear character of the characteristic of the assembly formed by the sensor and processing circuit 34 and which will become apparent from the detailed description of the circuit relative to FIGS. 2 to 4.

Figure 2:
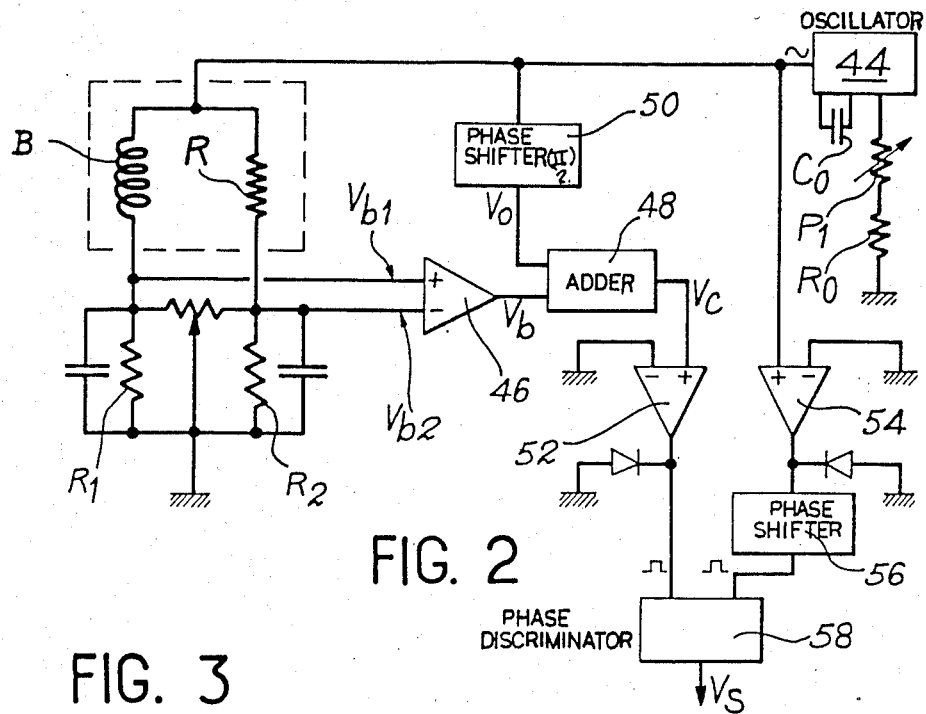
FIG. 2 the proximity processing circuit of the signal supplied by the eddy current probe in the apparatus of FIG. 1.

FIG. 2 shows the electronic processing circuit 34 of the signals supplied by the eddy current probe 10. This circuit makes it possible to carry out a differential phase measurement between the signal from coil B and a reference signal. This measurement is used for e.g. determining the distance separating the end of the probe from the facing surface.

In order to make it possible to detect variations in the impedance of probe coil B, the probe is placed with a reference resistor in a symmetrical measuring Wheatstone bridge, whose two branches $R_1$ and $R_2$ are used for balancing purposes. The thus formed measuring bridge is supplied between the high point defined by the junction of coil B with resistor R and the low point defined by the junction of branches $R_1$ and $R_2$ with a high frequency sinusoidal signal (e.g. 240 kHz) coming from a high frequency oscillator 44. The frequency of this sinusoidal signal is determined by a capacitor $C_0$ and a resistor $R_0+P_1$, in which $P_1$ is a variable resistance adjusted in such a way that coil B is at overvoltage resonance. The sinusoidal output signals $V_{b1}$ and $V_{b2}$ taken respectively at the common terminals of branches B and $R_1$ and R and $R_2$ are respectively transmitted to the positive terminal and the negative terminal of a differential amplifier 46, which supplies a sinusoidal signal $V_b$. This arrangement makes it possible to carry out a differential phase measurement between signal $V_{b1}$ from coil B and signal $V_{b2}$, which is proportional and in phase with the signal emitted by the oscillator. Signal $V_b$ is injected into an adder 48, with a signal $V_0$ corresponding to the signal injected into the measuring bridge by oscillator 44 and phase shifted by $(\pi/2)$ by a phase shifter 50. The sinusoidal signal $V_c$ supplied by adder 48 is injected into the positive terminal of a comparator 52, whose negative terminal is connected to earth. In the same way, the sinusoidal signal supplied by oscillator 44 is injected into the positive terminal of another comparator 54, whose negative terminal is also connected to earth. Comparators 52 and 54 supply positive logic signals for the positive half-cycles of the sinusoidal signals which are injected thereinto. The logic signal supplied by comparator 54 represents the positive half-signals of the sinusoidal signal supplied by oscillator 44. It is injected into a logic phase shifter 56 supplying a signal phase shifted by a given value compared with the input signal. This phase shifted signal is in turn injected into a phase discriminator 58 at the same time as the signal supplied by comparator 52, the latter representing the value of the signals at the terminals of coil B and resistor R. Phase discriminator 58 supplies a signal $V_s$ representing the phase difference between signal $V_{b1}$ supplied by coil B and the reference signal $V_{b2}$ linked with oscillator 44.

In summary, resistors R, R1 and R2 are chosen so that, when there is no eddy current, the bridge is equilibrated, i.e. $V_{b1}=V_{b2}$ in FIG. 2. When the coil is adjacent to a surface in which there are eddy currents, the impedance of the coil is modified and the bridge is no longer equilibrated, i.e. $V_{b1}\neq V_{b2}$; in particular, the phase of sinusoidal signal $V_{b1}$ is different from the phase of sinusoidal signal $V_{b2}$. The phase difference between these two signals is related to the modification of impedance of coil B. The difference between $V_{b1}$ and $V_{b2}$ is processed to deliver signal $V_s$ whose intensity is a function of this phase difference.

Figure 3:
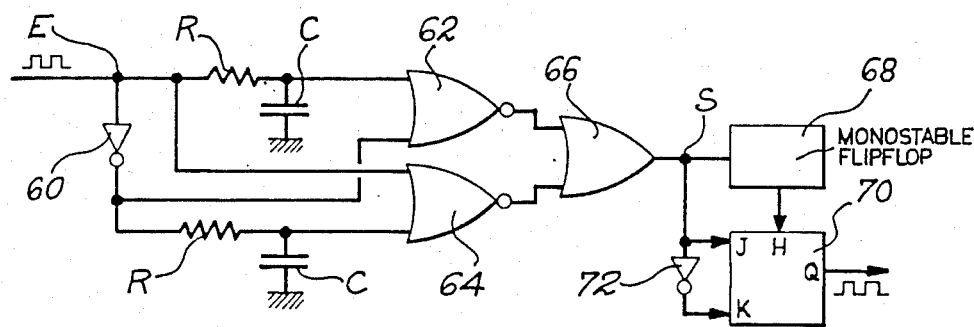
FIG. 3 the logic phase shifter circuit used in the processing circuit of FIG. 2.

As is shown in FIG. 3, the logic phase shifter 56 comprises an inverter 60 and two RC circuits make it possible to delay the signal injected at E into the phase shifter and the signal leaving inverter 60. The signal injected into the phase shifter and delayed by one of the RC circuits, as well as the circuit leaving inverter 60 are injected into a first NOR-gate 62. In the same way, the signal injected at E into phase shifter 56, as well as the signal leaving inverter 60 and delayed by the second RC circuit are injected into a second NOR-gate 64. The signal supplied by each of the NOR-gates 62 and 64 are injected into an OR-gate 66, which at S supplies a logic signal, whereof each pulse corresponds to the start and finish of a square-wave pulse of the signal injected at the input E of phase shifter 56. This logic signal is injected into the input of a monostable device 68, into the input J of flip-flop JK 70 and, via an inverter 72, into the input K of the latter. The output signal from the monostable device 68, which corresponds to a sequence of square-wave pulses of given duration starting with a given time lag compared with each pulse of the signal supplied at S, is injected into the input H of flip-flop JK, whereof the output signal supplied at Q is identical to the signal injected into the input E of the phase shifter, but phase shifted in accordance with a given value by the time lag imposed by monostable device 68. This output signal is injected into phase discriminator 58.

Figure 4:
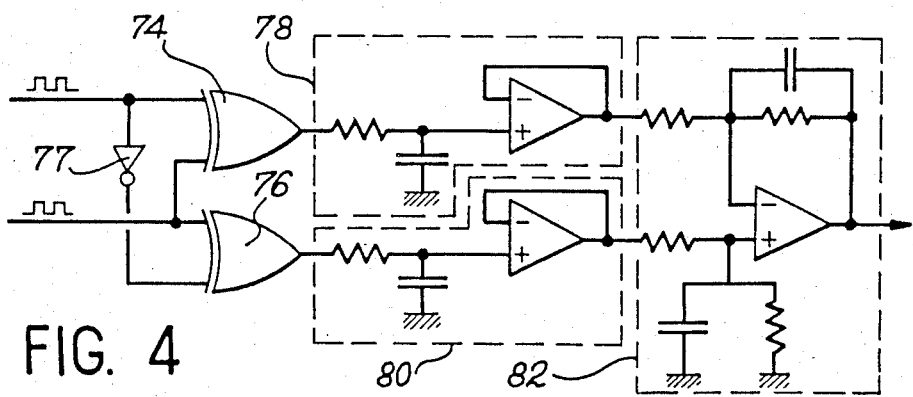
FIG. 4 the phase discriminator circuit used in the processing circuit of FIG. 2.

As is shown in FIG. 4, the two inputs of the phase discriminator 58 are connected on the one hand to an EXCLUSIVE-OR gate 74 and on the other to an EXCLUSIVE-OR gate 76 after the signal from the logic phase shifter 56 has passed through an inverter 78. The output of each of the EXCLUSIVE OR-gates 74, 76 is connected to an integrator 78, 80, whose output signals representing the direct current component of each of the signals injected at the phase discriminator input, are injected into a subtractor 82 supplying the d.c. output signal $V_s$, whose value corresponds to the phase difference between the signals supplied by phase shifter 56 and the signal from comparator 52.

Figure 5:
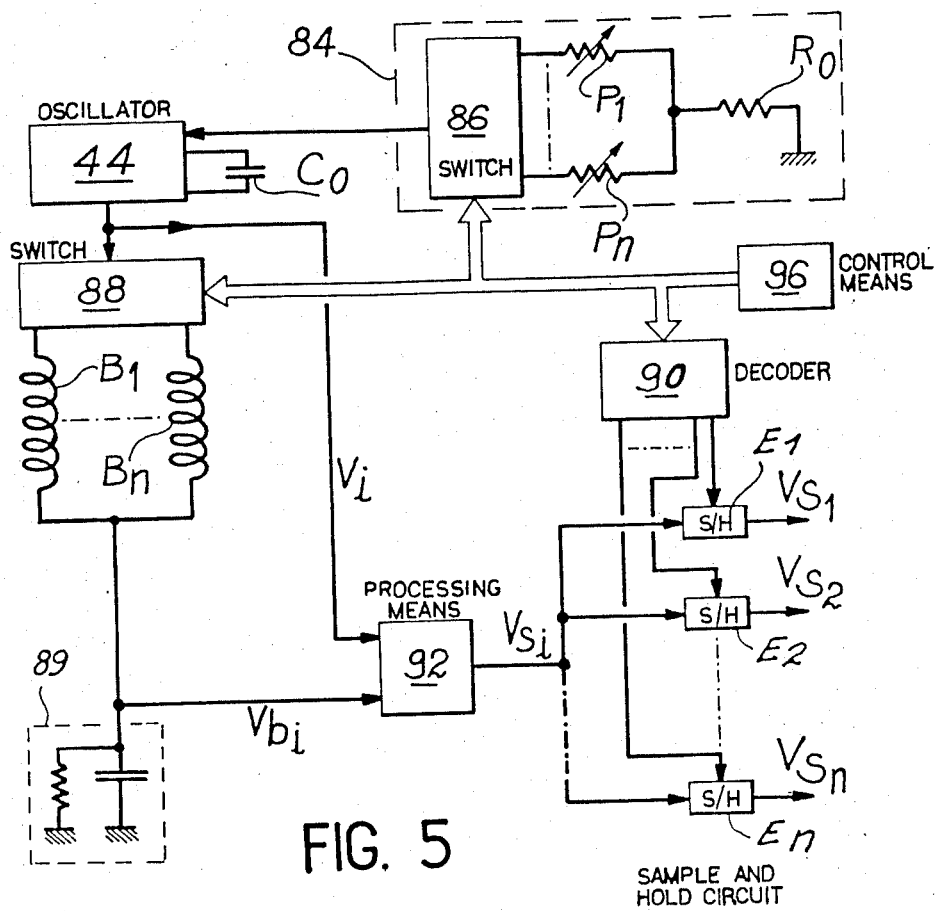
FIG. 5 a processing and sampling circuit according to the invention for an eddy current probe having a number n of coils.

FIG. 5 shows the processing and balancing circuit of an eddy current probe having n coils $B_1$, $B_n$ and a single processing means. The oscillator—coil connection is multiplexed. One terminal of each coil is interconnected to a single resistance—capacitance network 89 and to processing means 92.

Each of the coils $B_1 \ldots B_n$ is sequentially excited by a high frequency oscillator 44. The frequency of this high frequency oscillator 44 is determined for each coil by the value of a capacitor $C_0$ and by the value of a resistor fixed by the regulating means 84, incorporating a switch 86 having one output and n inputs, each being connected to a regulating unit $P_i$, in which $1 \leq i \leq n$, constituted by a variable resistor in series with a common resistor $R_0$.

The regulating unit and the resistance—capacitance network 89 form the blancing circuit.

The sinusoidal electric signal $V_i$ for coil i from high frequency oscillator 44 is injected into a switch 88, whereof each of the n outputs is connected to one end of each of the coils $B_1$ to $B_n$. The switching of the sinusoidal signal $V_i$, sequentially on each of the outputs of switch 88, takes place by a control means 96.

The sinusoidal signal $V_{bi}$ measured at the terminal of coil $B_i$ is passed to the processing means 92, in accordance with the circuits of FIGS. 2, 3 and 4. The processing means 92 also receives the sinusoidal signal $V_i$ from high frequency oscillator 44, apart from sinusoidal signal $V_{bi}$. It determines the phase difference between these two signals and supplies at the output a continuously variable electric signal $V_{Si}$, which takes account of the distance between the end of coil $B_i$ and the surface, whose distance from coil $B_i$ is to be measured. Different processing operations can be carried out on signal $V_{Si}$.

For example, as in the case of the drawing, it can be injected into the ith of the n sampling and maintaining means $E_1, E_2 \ldots E_n$. It can also be injected into an analog—digital converter for injection into a circuit or into a digital memory. The sampling control of one of the sampling and maintaining circuits $E_1, E_2 \ldots E_n$ takes place by means of a decoder 90 having n outputs, each connected to a sampling and maintaining circuit $E_1, E_2 \ldots E_n$ and receiving at the input the control signals from control means 96.

The circuit of FIG. 5 functions as follows. Control means 96 activates the first channel of each switch 86, 88 and the decoder 90, i.e. the input of switch 86 is switched on to the regulating unit $P_1$, the output of switch 88 on to coil $B_1$, the output of decoder 90 on to sample and hold circuit $E_1$. This control means can be constituted by a clock incrementing a coder, which addresses the switches 86, 88 and the decoder 90. Coil $B_1$ is then electrically supplied by the high frequency oscillator 44. The frequency of the signal supplied to coil $B_1$ is a function of the value of the regulating unit $P_1$. The latter has been previously regulated in such a way that coil $B_1$ is at overvoltage. The voltage $V_{b1}$ at the terminals of coil $B_1$ has a phase displacement with the signal $V_1$ supplied by high frequency oscillator 44, whose evaluation gives information on the distance from coil $B_1$ to the facing surface. The value of this phase displacement is represented by signal $V_{S1}$, which is sampled and maintained in the first sample and hold circuit $E_1$. After a time which is at least five times the cycle of the oscillator, the address supplied at the output of control means 96 is incremented so as to position switches 86, 88 and decoder 90 on coil $B_2$ and the regulating unit $P_2$ and the samplign and maintaining circuit $E_2$. Voltage $V_{b2}$ at the terminals of $B_2$ and the reference voltage $V_2$ are then injected into the processing means 92, which supplies signal $V_{S2}$. This signal is received in the second sampling and maintaining means $E_2$. The control means 96 sequentially addresses in the same way each of the other coils $B_3 \ldots B_n$.

It is possible to exploit the signals $V_{Si} \ldots V_{Sn}$ in various ways. If the coil is used in proximity, the sequence of signals makes it possible to e.g. reconstitute the profile of the analyzed surface. If it is wished to carry out a differential measurement between the signals from the juxtaposed coils, e.g. to evaluate the slope of a surface, a differential processing is carried out on the signals. Any other combination, which may or may not be linear, which may be in real time or delayed time, is possible on these signals, because they are stored in the sampling and maintaining means $E_1, E_2 \ldots E_n$.

The circuit according to FIG. 5 supplies each coil with a signal having a frequency appropriate for each coil. It must be ensured that the different excitation frequencies of the coils do not lead to a different sensitivity of the processing means 92, which would be prejudicial to the validity of the measurements.

Figure 6:
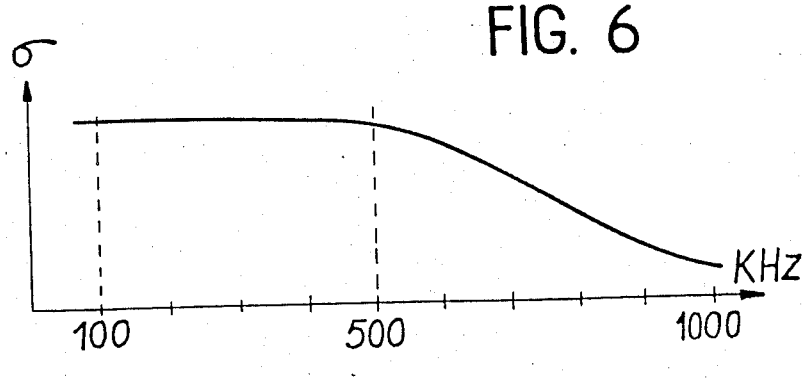
FIG. 6 the curve of the sensitivity variation of the phase measurement as a function of the frequency of the signal applied to the coil.

FIG. 6 shows the sensitivity curve of the phase measurement as a function of the excitation frequency of the coils. This sensitivity is roughly constant for a frequency range of between 100 and 500 kHz. The frequency adjustments necessary for the balancing of the coils is approximately 10 to 20% of the mean excitation frequency of the coils. By choosing a mean excitation frequency of 300 kHz, it would appear from the curve of FIG. 6 that operation at constant sensitivity takes place on varying by ±20% from this mean value.

This curve was plotted with a processing circuit 92 according to FIGS. 2 to 4. Identical results would be obtained with other circuits processing a signal which is a function of the phase difference between the signal measured at the terminals of the coil and a reference signal. Moreover, the frequency of the oscillator is fixed by the resistance—capacitance product RC, so that the regulation can also be carried out according to the invention on the basis of a common resistance $R_0$, a common capacitance $C_0$ and regulating capacitances $C_i$ for each coil i.

What is claimed is:

1. A multiple coil eddy current probe comprising:
    a plurality of coils ($B_1, \ldots, B_n$), each coil having a first terminal and a second terminal;
    a high frequency oscillator (44) having an output supplying a high frequency reference signal ($V_i$) to each first terminal of said coils, said oscillator having a control input for controlling the frequency of the signal ($V_i$) supplied by said oscillator;
    at least one processing means (92) to process a signal ($V_{bi}$) supplied by the second terminal of each of said coils when the first terminal of said each coil is connected to the output of said oscillator, said processing means receiving also the reference signal ($V_i$) and producing a processed signal ($V_{Si}$) for each of the coils which is a function of the phase difference between the signal ($V_{bi}$) supplied by each of the coils and the reference signal ($V_i$).
    at least, one storage means ($E_1, \ldots, E_n$) for storing each processed signal ($V_{Si}$) supplied by the processing means (92);
    a balancing circuit (84, 89) comprising at least a two terminal resistor—capacitor network (39) having one terminal grounded, and a regulating means (84) for regulating the high frequency signal, said balancing circuit being used to tune each of said coils to overvoltage or resonance, the second terminal of each of said coils being connected to the nongrounded terminal of said resistor—capacitor network and to an input of said processing means, switching means (88, 90); and
    control means (96), said control means controlling said switching means to sequentially connect the first terminal of each coil to the output of the oscillator, and to connect the output of said processing means to the input of a respective one of said storage means, said regulating means (84) being connected to the said control input of said oscillator, said regulating means being responsive to said control means for controlling the frequency of the signal supplied by the oscillator to each of said coils individually, so that the coil then connected to said oscillator is tuned to overvoltage or resonance.

2. An apparatus according to claim 1, wherein said regulating means comprises a plurality of regulating devices ($P_1, \ldots, P_n$) and a switching means, each regulating device being associated with a coil ($B_i$) and controlling the frequency of the signal supplied by the oscillator, so that said coil is tuned to overvoltage or resonance when connected to said oscillator, said switching means being controlled by said control means to connect, to the control input of the oscillator, the regulating device associated with the coil of which the first terminal is then connected to the output ($V_i$) of the oscillator.

3. An apparatus according to claim 2, wherein the regulating devices are variable resistors.

4. An apparatus according to claim 2, wherein the regulating devices are variable capacitors.

5. An apparatus according to claim 1, wherein the switching means emit a sequential addressing of the coils.

6. An apparatus according to claim 1, wherein there is only one processing means.

7. An apparatus according to claim 1, wherein said coils are in juxtaposed relation relative to each other.

8. An apparatus according to claim 1, wherein said coils are positionable in adjacent relation to the surface of a structure to determine the profile of said surface.

* * * * *

UNITED STATES PATENT AND TRADEMARK OFFICE
CERTIFICATE OF CORRECTION

PATENT NO. : 4,651,093

DATED : March 17, 1987

INVENTOR(S) : Jean-Marie Detriche et al.

It is certified that error appears in the above-identified patent and that said Letters Patent is hereby corrected as shown below:

Column 8, line 40, claim 1, change "(39)" to --(89)--.

Signed and Sealed this

Thirteenth Day of October, 1987

Attest:

DONALD J. QUIGG

*Attesting Officer*  *Commissioner of Patents and Trademarks*